United States Patent
Franzen

(10) Patent No.: US 8,253,095 B2
(45) Date of Patent: Aug. 28, 2012

(54) HIGH-RESOLUTION ION MOBILITY SPECTROMETRY

(75) Inventor: Jochen Franzen, Bremen (DE)

(73) Assignee: Bruker Daltonik GmbH, Bremen (DE)

(*) Notice: Subject to any disclaimer, the term of this patent is extended or adjusted under 35 U.S.C. 154(b) by 117 days.

(21) Appl. No.: 12/883,885

(22) Filed: Sep. 16, 2010

(65) Prior Publication Data

US 2011/0062322 A1 Mar. 17, 2011

(30) Foreign Application Priority Data

Sep. 17, 2009 (DE) .................. 10 2009 050 041

(51) Int. Cl.
*B01D 59/44* (2006.01)
(52) U.S. Cl. ........ 250/282; 250/281; 250/288; 250/290; 250/293
(58) Field of Classification Search .................. 250/281, 250/282, 288, 290, 293
See application file for complete search history.

(56) References Cited

U.S. PATENT DOCUMENTS

| 7,514,676 B1 | 4/2009 | Page et al. |
| 8,080,787 B2 * | 12/2011 | Rather et al. .................. 250/290 |
| 2010/0090102 A1 | 4/2010 | Rather et al. |

FOREIGN PATENT DOCUMENTS

WO 2004/109741 12/2004

* cited by examiner

*Primary Examiner* — Michael Maskell
(74) *Attorney, Agent, or Firm* — O'Shea Getz P.C.

(57) ABSTRACT

A supersonic gas jet having gas molecules with substantially equal velocities is formed by directing the gas through a Laval nozzle into an evacuated chamber. A field barrier having a substantially constant height across a cross-section of the supersonic gas jet is formed by respectively applying potentials $U_2$, $U_3$ and $U_4$ to an arrangement of three apertured diaphragms $R_2$, $R_3$ and $R_4$, which are respectively separated by distances $d_2$ and $d_3$, where $(U_4-U_3)/(U_3-U_2)=d_3/d_2$. The ions in the supersonic gas jet are directed against the field barrier, where ions with a mobility below a mobility threshold are pushed over the field barrier, and where ions with a mobility higher than the mobility threshold are held back by the field barrier.

14 Claims, 6 Drawing Sheets

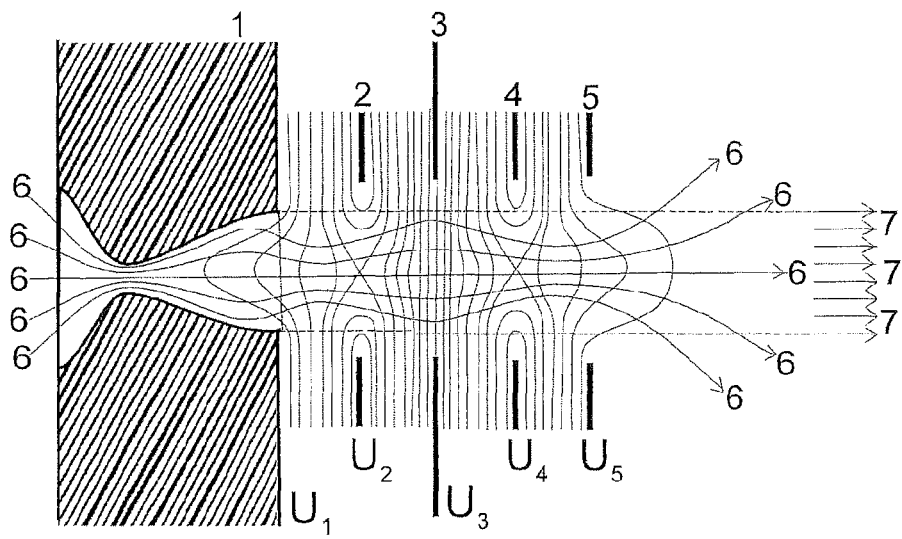
FIG. 2A
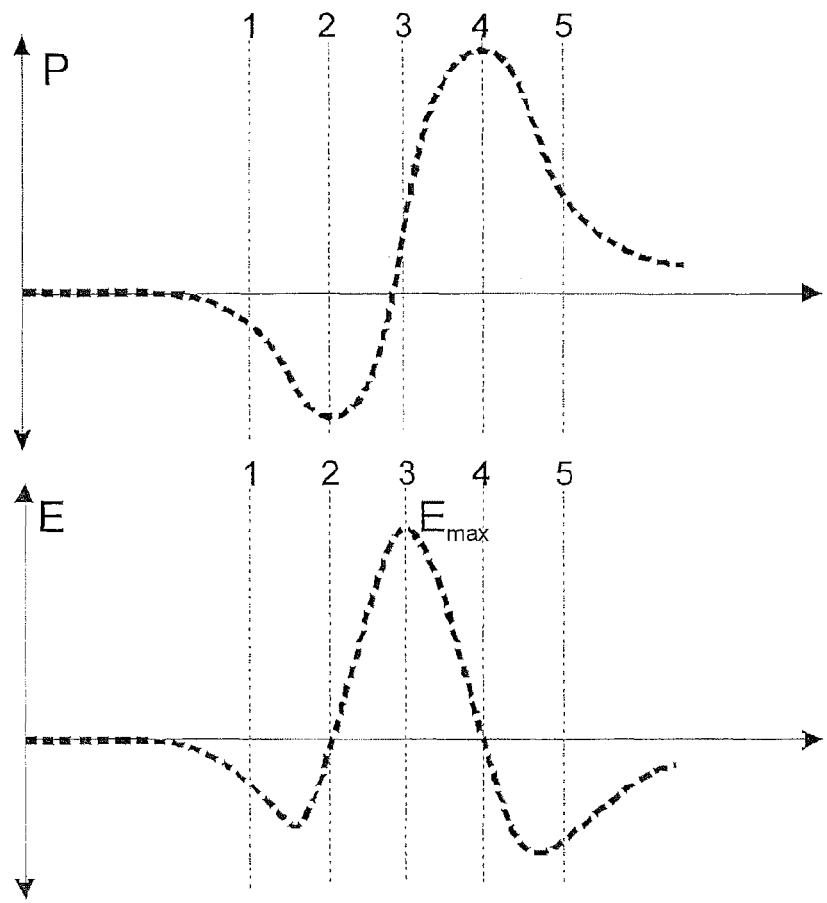
FIG. 2B
FIG. 2C

HIGH-RESOLUTION ION MOBILITY SPECTROMETRY

PRIORITY INFORMATION

This patent application claims priority from German Patent Application No. 10 2009 050 041.3 filed on Sep. 17, 2009, which is hereby incorporated by reference.

FIELD OF INVENTION

The present invention relates generally to measuring ion mobilities in gas that moves against a field barrier.

BACKGROUND OF THE INVENTION

A typical mass spectrometer is used for determining mass-to-charge ratios of sample ions. The term "mass-to-charge ratio" refers to the ratio of a mass m of the ion to a dimensionless number of elementary charges z of the ion. This charge-related mass m/z therefore has a physical dimension of a mass. In the following disclosure, the term "mass-to-charge ratio" may also be referred to using the terms "mass of an ion" or an "ion mass".

The term "ion species" refers to ions having substantially identical elemental compositions, charges and three-dimensional structures. An ion species generally includes all the ions of an isotope group. While ions in the isotope group may have slightly different masses, they typically have substantially equal mobilities.

Isomers of a primary structure of bioorganic molecules (i.e., structural isomers) and isomers of a secondary or tertiary structure (i.e., conformational isomers) typically have substantially equal masses, but different geometrical forms. It is therefore practically impossible to differentiate structural and conformational isomers as a function of their mass. Some information regarding an isomeric structure can be obtained using fragment ion mass spectra. A more efficient and certain method to identify and distinguish isomers, however, is to separate the isomers according to their different ion mobilities.

Today, ion mobilities are predominantly obtained by measuring ion drift velocities in long drift regions under influence of an electric field. A typical drift region for measuring ion mobility includes an inert gas (e.g., helium or nitrogen) disposed therein. Sample ions (i.e., ions of the substance under investigation) are pulled through the gas by the electric field. The electric field is generated, for example, by DC potentials on ring electrodes that line the drift region. A large number of collisions with gas molecules provide each ion species with a relatively constant drift velocity $v_d$ that is more or less proportional to the electric field strength E:

$$v_d = K_0 \times E.$$

The proportionality factor $K_0$ may be referred to as the "ion mobility" of an ion species. The ion mobility is a function of temperature, gas pressure, type of gas, ionic charge and the collision cross-section of the ions.

Isomeric ions with the same charge-related masses m/z and different collision cross-section typically have different ion mobilities at the same temperature, pressure and type of gas. Isomers with the smallest geometric dimensions typically have the greatest mobility and therefore the highest drift velocity through the gas. Unfolded protein ions, for example, undergo more collisions than tightly folded protein ions. Protein ions which are unfolded or partially folded therefore arrive at the end of the cell later than strongly folded ions of equal mass. Structural isomers (e.g., proteins with glycosyl, lipid or phosphoryl groups at different sites), however, also have different collision cross-sections, which allow them to be distinguished by measuring their ion mobility.

Under conditions when the electric fields E are relatively strong, the electric field strength equation is provided as follows:

$$v_d = K_0 \times E + K_1 \times E^2.$$

The factor $K_1$ indicates how the collision cross-section changes under the influence of the electric field. The constant $K_1$, however, is typically so small that it can be ignored. Precision measurements of the mobility $K_0$ should account for this dependence. It is typically advantageous therefore to carry out precision measurements at low field strengths.

The folding structures of ions, which can be identified via their mobility, have become increasingly important during chemical and biological research. Devices for measuring the mobility of ions therefore have been incorporated into mass spectrometers in order to combine the measurements of the charge-related mass of ions with measurements of collision cross-sections. The folding structures determine the mechanism of action and thus the function of the molecules in the living organism. Different folding, for example, can signify normal or abnormal functioning of biopolymers in biosystems, and hence health or disease of tissue parts or even whole organisms.

Several academic research groups have coupled ion mobility spectrometers with mass spectrometers. In such systems, the mobility drift region typically has a pressure range of several hectopascals, a length of four or more meters for higher mobility resolutions, and electric field strength of 2,000 or more volts per meter. In this pressure range, the drifting ions do not form many complexes with other substances. The mobilities of the ion species therefore can be measured without interferences, unlike mobility measurements at atmospheric pressure. Long drift regions, however, typically have relatively large diameters because the ions diffuse radially over long distances.

The ions are typically introduced into the drift region by temporally short ion pulses. The ions initially take the shape of spatially small ion clouds, which are pulled through the drift region by the electric field. In the gas of the drift region, the ion clouds are diffused into the surrounding space by collisions statistically distributed by spatial directions and kinetic energies due to the molecular Brownian motion. The diffusion takes place in both a forward and backward direction, and also at right angles to the drift direction. The gas in the drift region is maintained, for example, at a temperature between approximately 150 and 300 degrees Celsius. Alternatively, the gas in the drift region may be cooled for special experiments.

The mobility resolving power (hereinafter "mobility resolution") is defined as:

$$R_{mob} = K_0/\Delta K_0,$$

where $\Delta K_0$ is the width of the ion signal of the mobility $K_0$ at half height, measured in units of the mobility. The mobility resolution $R_{mob}$ is influenced predominantly by the diffusion broadening of the ion clouds, especially for long drift regions and high electric field strengths. Other influences, such as the space charge, tend to be negligibly small. The part of the mobility resolution determined by the diffusion broadening is defined as:

$$R_d = \sqrt{\frac{zEL_d}{kT\ln 2}},$$

where z is the number of elementary charges e, E the electric field strength, $L_d$ the length of the drift region, k the Boltzmann constant, and T the temperature of the gas in the drift region. A high mobility resolution may be achieved using a high field strength E, long drift regions $L_d$, or low temperatures T. The part $R_d$ of the mobility resolution that is given by the diffusion is independent of the type and pressure of gas in the drift region. The mobility $K_0$ itself, however, is dependent on the temperature, the pressure and the type of gas in the drift region.

Compared to the numerical values for mass resolutions in mass spectrometry, the mobility resolutions that are achieved in practice are generally relatively low. Typically, commercial ion mobility spectrometers for bioorganic ions have mobility resolutions of $R_{mob}$ equal to 10 to 15. With a mobility resolution of $R_{mob}=10$, two ion species whose collision cross-sections differ by only 20 percent can be separated relatively well.

Some highly specialized academic groups have been able to achieve significantly higher mobility resolutions of between $R_{mob}$ between 60 and 100, and in rare individual cases up to $R_{mob}$ equal to 150, with drift lengths roughly between two and six meters and field strengths between approximately 2,000 and 4,000 volts per meter. Under these conditions, ion species whose mobilities differ by merely one to three percent may be differentiated. Hereinafter, the term "high resolution" shall refer to resolutions of $R_{mob}$ above 60.

A strong transverse diffusion may also occur in long mobility drift regions. Longer drift regions therefore should have a large diameter such that the ions do not touch the wall electrodes. The ions may be guided back to the axis of the drift region after having travelled approximately two meters through the drift region. This is accomplished using an "ion funnel". An ion funnel includes a plurality of parallel ring diaphragms, where each diaphragm is separated from adjacent diaphragms by a relatively small distance (e.g., in the order of millimeters). The ring diaphragms have aperture diameters that continuously taper from the diameter of the drift region (e.g., 30 to 40 centimeters) down to around two to five millimeters, which forms a funnel-shaped enclosed volume. The two phases of an RF voltage, usually of several megahertz and between a few tens of volts and one hundred volts, are applied alternately to the apertured diaphragms, thus generating a pseudopotential that keeps the ions away from the funnel wall. A DC electric field is superimposed on the RF voltage by a DC voltage gradient. The electric field pushes the ions slowly towards and then through the narrow exit of the funnel. Alternatively, such an ion funnel does not measurably reduce the mobility resolution of a long drift region.

Ion funnels are also used in mass spectrometers to capture larger ion clouds and to thread these ion clouds into narrow ion guides. Referring to FIG. 5, ion funnels are often found in mass spectrometers with electrospray ion sources. The ions generated outside the vacuum system are transferred, together with a curtain gas, through inlet capillaries and into the vacuum. The ions are then captured by ion funnels and freed of most of the curtain gas. Some mass spectrometers may include two ion funnels, placed in series, in order to move the ions quickly from regions with higher pressure of several hectopascals at the end of the inlet capillary to regions with lower pressure of around $10^{-2}$ to $10^{-6}$ pascal.

High-resolution time-of-flight mass spectrometers with perpendicular injection of the ions (OTOF-MS), for example, have successfully been combined with mass spectrometers. Disadvantageously, however, such high-resolution ion mobility spectrometers are typically several meters long and, thus, are not commercially viable. Even ion mobility spectrometers having a straight drift region with moderate resolutions are approximately one meter long.

There is a need for a high resolution ion mobility spectrometer.

SUMMARY OF THE INVENTION

The present invention includes methods and devices for generating (a) a gas jet having molecules with substantially equal velocities and (b) a field barrier having a substantially uniform height across the cross-section of the gas jet. Under these conditions, the ions in the gas can be sorted according to their mobilities with a high mobility resolution. The gas jet is generated using a sharply focused supersonic gas jet from a Laval nozzle. Such a supersonic gas jet has a low temperature of a few Kelvin, a low pressure and substantially equal velocities for the molecules, with only a relatively small statistical variance in the velocity due to the low temperature. The field barrier is generated by applying suitable voltages on at least three thin apertured diaphragms. Where, for example, the apertured diaphragms $R_2$, $R_3$ and $R_4$ have the same aperture diameter, are separated by distances $d_2$ and $d_3$ respectively, and have potentials $U_2$, $U_3$ and $U_4$ applied to them, a field barrier with uniform height can be generated in the middle aperture diaphragm across the entire apertured diaphragm when the relation $(U_4-U_3)/(U_3-U_2)=d_3/d_2$ is maintained.

The ion mobility spectra are acquired by measuring the current of the ions that are pushed over the field barrier in the apertured diaphragm $R_3$ by the supersonic gas jet. The ions are pushed as a function of the height of the voltage $V=(U_4-U_2)$ at the apertured diaphragms, which is proportional to the height of the potential barrier. During this process, the ions are constantly replenished by the ion source. When the field barrier is changed continuously or incrementally, a total ion current curve is measured at the ion detector. The total ion current curve represents an integral over the mobility spectrum. Differentiation of the total ion current curve with respect to the height of the potential barrier provides the mobility spectrum of the ions. The method of acquiring mobility spectra may be calibrated using ions of known mobility. The mobilities of the ions can be derived from calibrated mobility spectra.

The ion current may be measured and separated according to mass by a mass analyzer, in the form of a series of mass spectra as a function of the height of the voltage $V=(U_4-U_2)$ at the apertured diaphragms, using, for example, a time-of-flight mass spectrometer with orthogonal ion injection. Individual ion current curves for ions of individual mass ranges may then be derived from the series of mass spectra. Differentiating the individual ion current curves provides ion mobility spectra for individual mass ranges. The mass ranges can cover ions of several masses, such as the masses of an isotopic group, or ions of a single mass.

The present method provides a relatively good mobility resolution of $R_{mob} \geqq 100$ because, in initial experiments without a Laval nozzle and without a field barrier of uniform height, mobility resolutions of more than $R_{mob}=40$ have already been achieved.

These and other objects, features and advantages of the present invention will become more apparent in light of the following detailed description of preferred embodiments thereof, as illustrated in the accompanying drawings.

BRIEF DESCRIPTION OF THE DRAWINGS

FIG. 2A schematically illustrates an apparatus for dividing ions as a function of ion mobility;

FIG. 2B graphically illustrates a potential profile P through an axis of the apparatus in FIG. 2A;

FIG. 2C graphically illustrates a characteristic of strength of an opposing electric field E;

DETAILED DESCRIPTION OF THE INVENTION

The present invention includes methods and devices for generating a gas jet having molecules and ions with substantially equal velocities, and erecting a field barrier having a substantially uniform height across a cross-section of the gas jet. Ions in gases may be sorted according to their mobility with a high sorting limit resolution. The gas jet is used to push ions with mobilities below a mobility threshold over the field barrier. The field barrier is used to sharply reject those ions with mobilities above the mobility threshold. The field barrier, as indicated above, is the steepest rise of an electric potential barrier.

Figure 1:
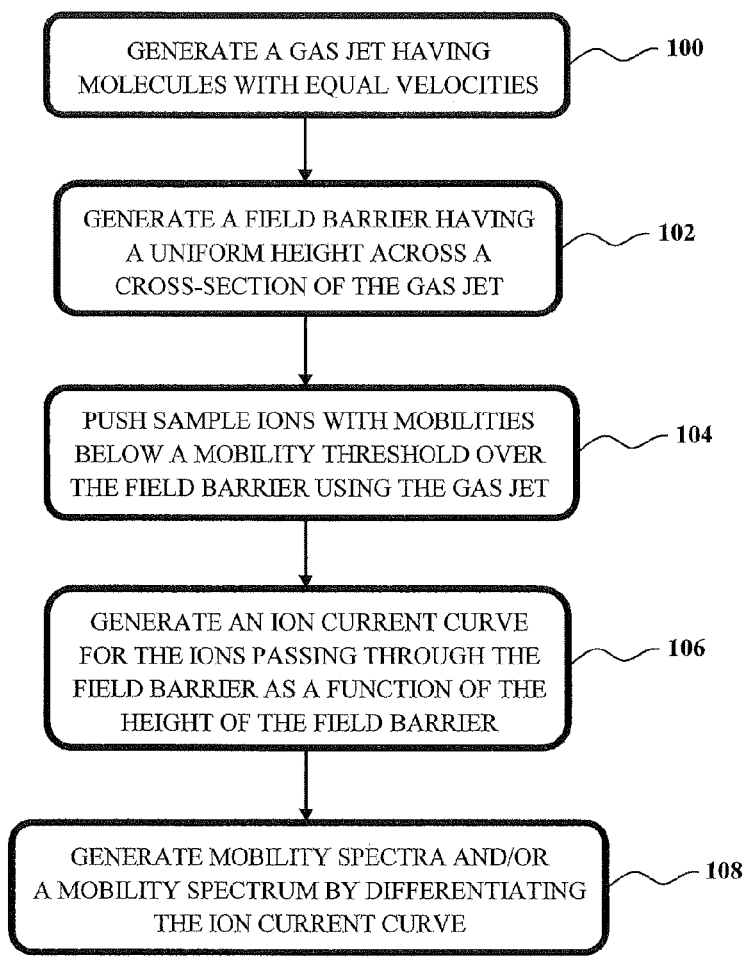
FIG. 1 is a flow diagram of a method for generating mobility spectra of sample ions.

Referring to FIG. 1, in step 100 the gas jet is formed by a sharply focused supersonic gas jet of molecules and ions with substantially equal velocities, which is generated by a suitably shaped Laval nozzle. The supersonic gas jet has a relatively low temperature (e.g., a few Kelvin) and a low pressure. The velocities of the molecules have relatively small statistical variances as a result of the low temperature. Where the Laval nozzle is correctly shaped (i.e., shaped in such a manner as to generate a jet of molecules and ions with substantially equal velocities), the supersonic gas jet has a substantially constant cross-section over a length of at least a few centimeters, and the molecules fly in parallel. The optimum form of the Laval nozzle can be constructed using, for example, a method of characteristics known from gas dynamics. For air, the molecules can achieve a maximum velocity of v equal to $792\sqrt{(T_0/293K)}$ m/s, which are only slightly lower in practice.

Referring to FIGS. 1 and 2A, in step 102 the field barrier of uniform height is generated by a potential distribution across three or more apertured diaphragms. Where, for example, three thin apertured diaphragms $R_2$, $R_3$ and $R_4$ (i) have identical aperture radii $r_2$, $r_3$, and $r_4$, (ii) are respectively separated by distances $d_2$ and $d_3$, and (iii) have the potentials $U_2$, $U_3$ and $U_4$ respectively applied thereto, a field barrier with uniform height can be generated across the entire central apertured diaphragm $R_3$ when $(U_4-U_3)/(U_3-U_2)=d_3/d_2$. The height of the field barrier is proportional to the voltage V equal to $(U_4-U_2)$. Where the apertured diaphragms are relatively thick, or have different diameters, or where the external fields effect stronger asymmetrical field penetrations through the outer apertured diaphragms, the condition should be correspondingly corrected. In the simplest case of three equally separated identical apertured diaphragms 2, 3 and 4, $U_3=(U_4-U_2)/2=V/2$. The apertured diaphragms are formed from a mechanically thin, electrically conductive material such as, but not limited to, sheet metal.

Referring still to FIG. 2A, the Laval nozzle is disposed in a wall 1 between chambers having different pressures. The Laval nozzle, when appropriately shaped, generates a supersonic gas jet 7 having molecules with substantially equal velocities. The shape of the Laval nozzle may be designed or calculated using the method of characteristics, or by any other suitable methods of gas dynamics. In the interest of ease of illustration, the Laval nozzle is depicted larger than it really is for reasons of clarity. The potential of the Laval nozzle is designated hereinafter as $U_1$.

The three apertured diaphragms 2, 3 and 4 generate opposing electric fields with suitably applied potentials $U_2$ to $U_4$. In the apertured diaphragm 2, the above-mentioned voltage condition $U_3=(U_4-U_2)/2=V/2$ generates a field barrier having a substantially uniform height in a direction transverse to the supersonic jet. The height of the field barrier is proportional to the voltage V. The potential distribution is shown in FIG. 2A by thin equipotential lines. Several possible ion trajectories for ions of a given low mobility are shown via lines 6. The ion trajectories 6 illustrate that the ions are initially focused between the nozzle in the wall 1 and the apertured diaphragm 2 and then defocused, as far as their mobility allows. The ions are further defocused between the apertured diaphragms 2 and 3, and refocused between the apertured diaphragms 3 and 4. The voltage $(U_2-U_1)$ is selected such that the ions are focused, when possible, within the Laval nozzle, and do not hit the wall as a result of Coulomb repulsion when the mobility of the ions increases due to a fall in temperature and pressure. The focusing and defocusing are effective insofar as the mobility of the ions in the supersonic gas jet allows. The apertured diaphragm 5 makes the external field penetrations through the diaphragms 2 and 4 approximately symmetrical. The apertured diaphragms 2, 3 and 4 respectively correspond to the apertured diaphragms $R_2$, $R_3$ and $R_4$ with aperture radii $r_2$, $r_3$, and $r_4$ as referenced above.

Ions having high mobilities that push back against the supersonic gas jet by the field in front of the apertured diaphragm 3 are in a slightly defocusing field and therefore exit the supersonic gas jet in a lateral direction. Care should be taken that these ions do not reach the ion detector by, for example, extending the apertured diaphragm 3 radially outward to the chamber walls. Most of these ions are destroyed outside the jet at the apertured diaphragm 2, which is at an ion-attracting potential.

Figure 10:
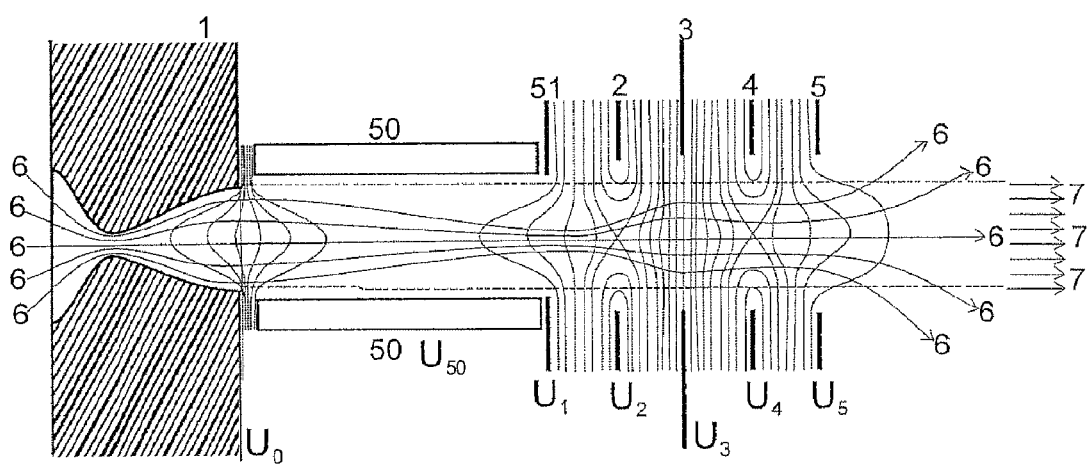
FIG. 10 diagrammatically illustrates another embodiment of an apparatus for dividing ions as a function of ion mobility.

The ion trajectories are illustrated in FIG. 2A in such a manner that no losses occur as a result of the ions prematurely leaving the supersonic jet. The trajectories, however, do not necessarily apply to all ions in the jet. For a qualitative analysis, the losses are acceptable. For a quantitative analysis, however, the losses are unacceptable. Referring to FIG. 10, a short quadrupole rod system operated at RF may be inserted between the Laval nozzle plate 1 and the first apertured diaphragm 2 to drive ions as efficiently as possible into and along the axis of the supersonic jet. The trajectories 6 of the ions in the supersonic gas jet 7 are focused into the axis of the supersonic gas jet 7 by the RF quadrupole rod system 50. In some embodiments, the quadrupole rod system 50 has a length of approximately two centimeters and is operated with a frequency of approximately two megahertz. Under these conditions, the ions experience approximately 50 periods of the RF voltage, which is in general sufficient for focusing.

The potential profile P through the axis of the arrangement in FIG. 2A is shown in FIG. 2B. By differentiating the potential profile, the profile of the opposing electric field E is obtained as shown in FIG. 2C, which has a peak in the apertured diaphragm 3 and has a uniform height across the apertured diaphragm.

Figure 3:
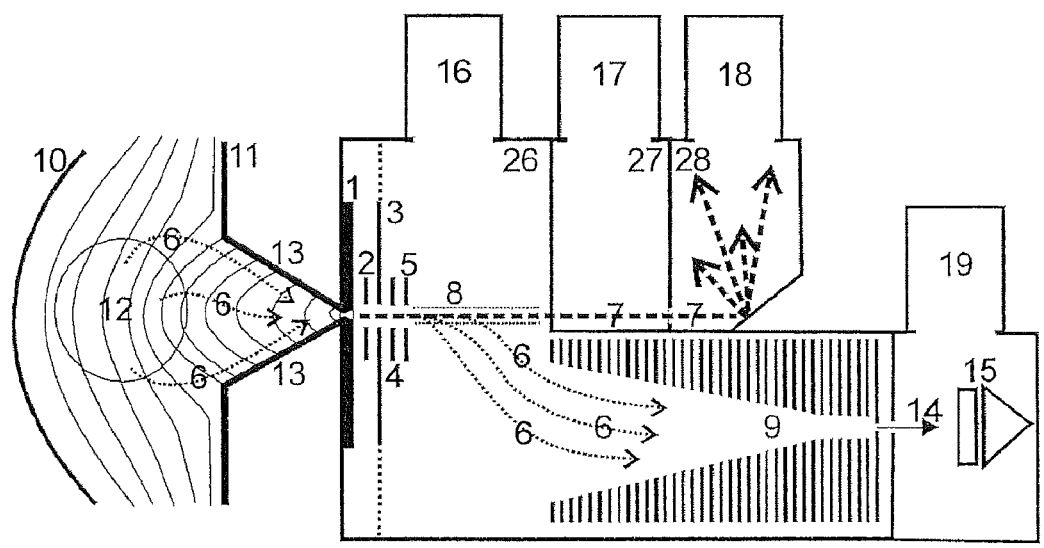
FIG. 3 diagrammatically illustrates an ion mobility spectrometer that includes the apparatus in FIG. 2A.

The apparatus in FIG. 2A can be included in a complete mobility spectrometer. Referring to FIG. 3, for example, ions from an ion cloud 12 at atmospheric pressure are guided along the ion trajectories to the Laval nozzle in wall 1. The Laval nozzle is therefore designed to accommodate (i) atmospheric pressure at the entrance and (ii) vacuum pressure of, for example, a few hectopascals at the exit. The ions with sufficiently low mobility that remain after passing over the field maximum are driven out of the supersonic gas jet by an electrode arrangement 8 and sent via an ion funnel 9 as an ion beam 14 to an ion detector 15. To prevent the gas from the supersonic gas jet from burdening a vacuum chamber 26, the supersonic gas jet, which has been freed of ions, is directed through a vacuum chamber 27 into a vacuum chamber 28, where it is refracted by impact. The gas thus achieves a higher pressure and can be pumped off by a pump 18 such as, but not limited to, a forepump.

Figure 4:
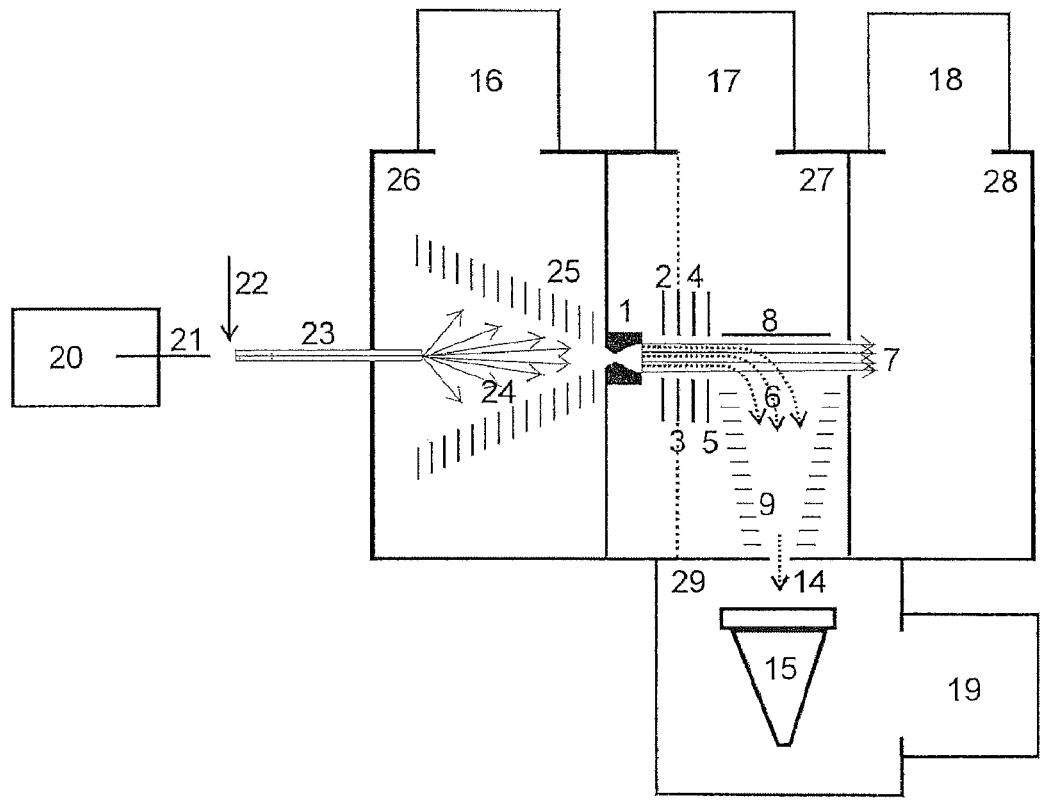
FIG. 4 diagrammatically illustrates another embodiment of an ion mobility spectrometer that includes the apparatus in FIG. 2A.

In some embodiments, the Laval nozzle can be operated, for example, at pressures of a few hectopascal or kilopascal. Referring to FIG. 4, a known electrospray ion source 20 is shown with a spray capillary 21, a feed 22 for heatable curtain gas and an inlet capillary 23. The diffuse outflow 24 from the inlet capillary 23 generates a pressure in the ion funnel 25 that operates the Laval nozzle in the wall 1. When the inlet capillary 23 is properly dimensioned, the pressure generated by the inlet capillary 23 can be a few kilopascal. The gas is initially cooled by adiabatic expansion in the input capillary 23. The cooled gas enters, as diffuse gas jet 24, into the chamber 26 with the ion funnel 25. Notably, the temperature of the gas is largely restored by gas friction. When an ambient temperature of approximately 293 Kelvin again prevails in the ion funnel 25, for example, the supersonic gas jet 7 can achieve a maximum velocity of 792 meters per second. When the restored temperature $T_0$ of the gas in the ion funnel 25 is lower than 293 Kelvin, the maximum velocity is smaller by the root of the ratio of the temperatures. The supersonic gas jet 7 is guided into a special pump chamber 28, as indicated above, from where its gas can be easily pumped off by a pump 18. A low pressure therefore can be maintained in the vacuum chamber 17, where the mobility separation takes place, such that the supersonic jet 7 is not hindered by the ambient gas.

Figure 9:
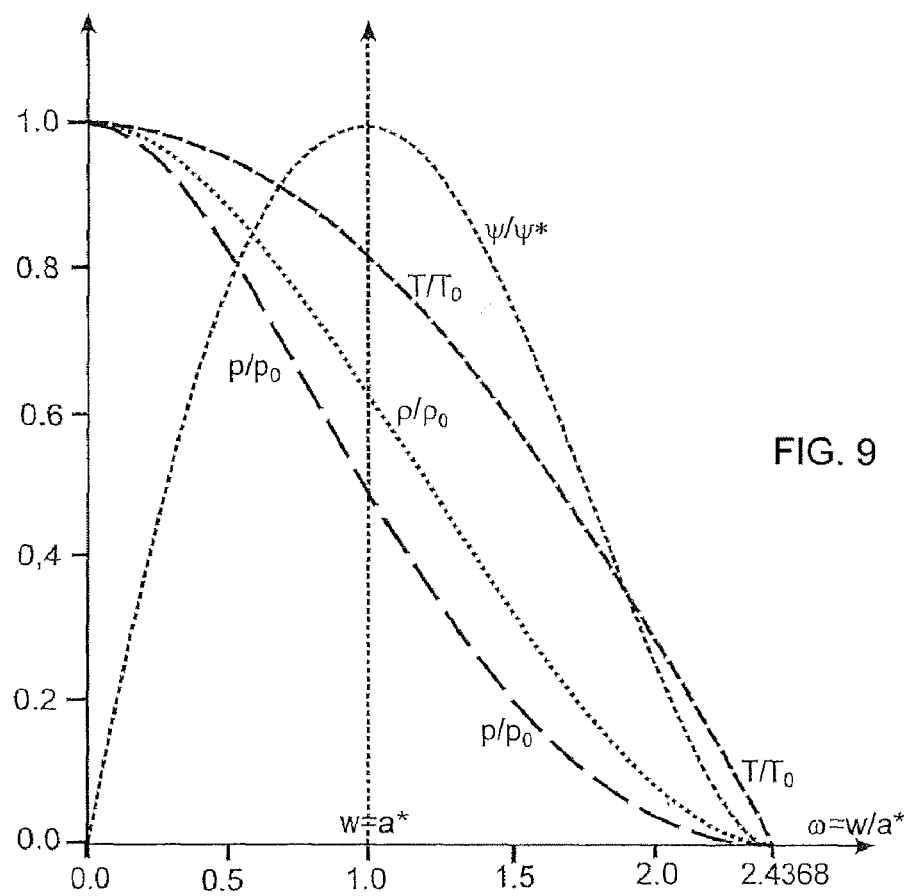
FIG. 9 graphically illustrates an "outflow diagram" for compressible gases (e.g., air) from a region with pressure $p_0$, density $\rho_0$ and temperature $T_0$.

Referring to FIG. 9, an outflow diagram is shown for a compressible gas (e.g., air) flowing from a high pressure region, with pressure $p_0$, density $\rho_0$ and temperature $T_0$, to a low pressure region. The local pressure $p/p_0$, local density $\rho/\rho_0$ and local temperature $T/T_0$ are plotted against the relative gas velocity $\omega$. The relative gas velocity $\omega$ is equal to the local gas velocity w divided by the local speed of sound a* in the narrowest cross-section of the Laval nozzle ($\omega$=w/a*). The curve of the flow density $\psi=\rho\times w$ is related to the flow density $\psi*$ in the narrowest cross-section. For the outflow of air, a maximum velocity of the supersonic gas jet $w_{max}$ is equal to approximately 2.4368 times the local speed of sound a*. The local speed of sound a* is equal to approximately 91.19 percent of the speed of sound in the gas in front of the Laval nozzle (i.e., at $T_0$). For outflowing air under standard conditions (e.g., 20° Celsius) the maximum velocity of the molecules of the supersonic gas jet is approximately 792 meters per second. For the outflow from a region of lower pressure it depends on the temperature $T_0$ of the lower pressure region, because the speed of sound is independent of the pressure, but proportional to the square root of the temperature.

The shape of a Laval nozzle can be optimized using, for example, the known aforesaid "method of characteristics". The Laval nozzle is substantially optimized for ambient pressure at the exit, the most favorable supersonic gas jet being generated when the pressure in the emerging supersonic gas jet is, for example, exactly equal to the ambient pressure. For a Laval nozzle operated at atmospheric pressure, as shown in FIG. 3, a key factor is the ratio of the diameter $d_a$ of the exit aperture to the diameter $d_e$ in the narrowest cross-section. The flow density curve in FIG. 9 shows that for an ambient pressure of one hectopascal, a diameter ratio $d_a/d_e$ of approximately 4.5:1 is advantageous. For a Laval nozzle measuring 0.5 millimeters at the narrowest cross-section, which generates an inflow of approximately 3.7 liters per minute, an exit aperture of approximately 2.5 millimeters diameter can be used to produce a supersonic gas jet having a 2.5 millimeter diameter. For Laval nozzles operated at far lower pressures different conditions may apply.

Figure 6:
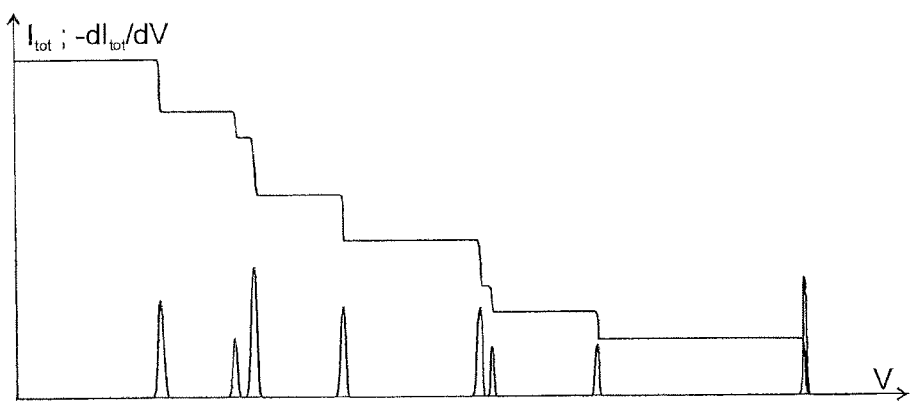
FIG. 6 graphically illustrates (i) an integral curve of a total ion current $I_{tot}$ of a mobility measurement as a function of voltage V (i.e., a field barrier height), and (ii) a mobility spectrum of a mixture of ions obtained by differentiating the integral curve $I_{tot}$ with respect to the voltage V.

Mobility spectra is measured in the arrangements shown in FIGS. 3 and 4 by continuously or incrementally varying the potential difference $V=(U_4-U_2)$, and with it the maximum of the axial field strength, rather than using field barriers kept on constant height. Given a substantially constant ion current from an ion source, therefore, more and more (or if the field barrier is lowered, fewer and fewer) ion species are filtered out at the field barrier due to their specific mobility. The ion current is thus measured in step 106 which forms the integral over the mobility spectrum of the ions. Differentiating the integral curves gives the mobility spectrum in step 108. FIG. 6 graphically illustrates the total ion current $I_{tot}=f(V)$ (the top curve) and the mobility spectrum $-dI_{tot}/dV=f'(V)$ (the bottom curve) obtained by differentiating with respect to V.

The mobilities of the ion species in a mixture of ions can be read from the mobility spectrum. The mobility spectrum does not, however, provide any indication of the masses of the ions, which provide information as to identity of the ion species.

Figure 5:
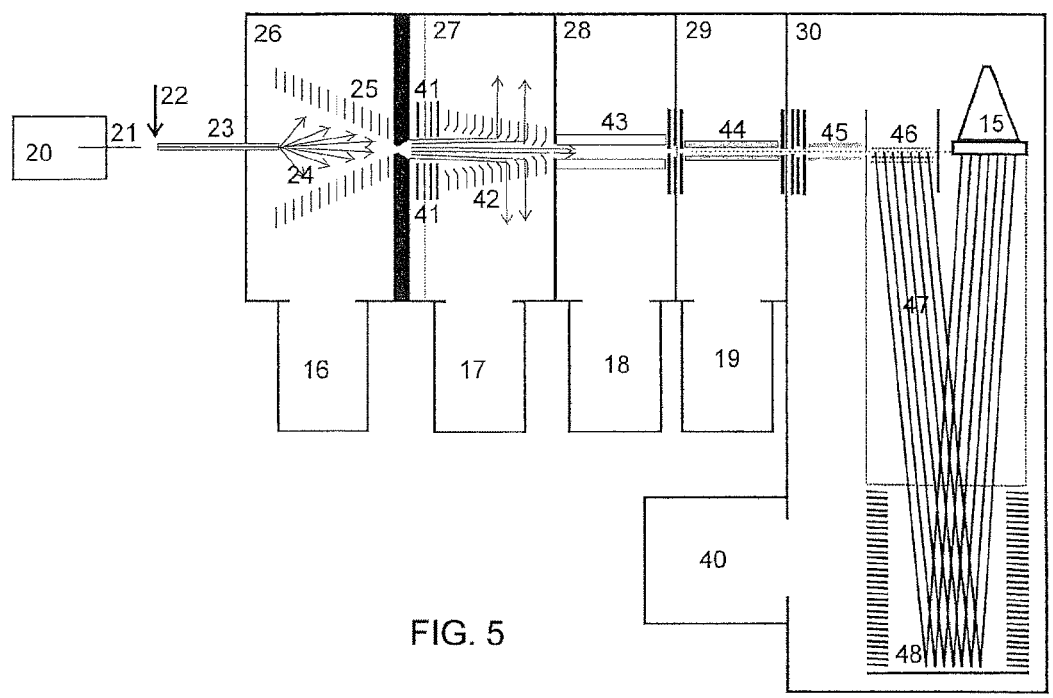
FIG. 5 diagrammatically illustrates a system that includes a time-of-flight mass spectrometer with orthogonal ion injection coupled to the ion mobility spectrometer in FIG. 4.

In order to obtain the masses of the ions, the input region of the mobility spectrometer in FIG. 4 can be coupled to a time-of-flight mass analyzer (e.g., a time-of-flight mass spectrometer with orthogonal ion injection), as shown in FIG. 5. The Laval nozzle plate and the four apertured diaphragms shown in FIG. 5 form a mobility filter 41. The ions that pass the mobility filter 41 are collected by an ion funnel located in the axis of the supersonic gas jet and are guided via ion guides 43, 44 and 45 to a pulser 46. The pulser 46 pulses out a segment of the ion beam perpendicular to the previous direction of flight, and forms an ion beam 47. The ion beam 47 is reflected in an energy-focusing reflector 48, and the mass spectrum is measured by an ion detector 15. The differential pumping system includes the vacuum chambers 26 to 29, which are evacuated by the pumps 16 to 19. The flight tube 30 is evacuated by a pump 40.

Figure 7:
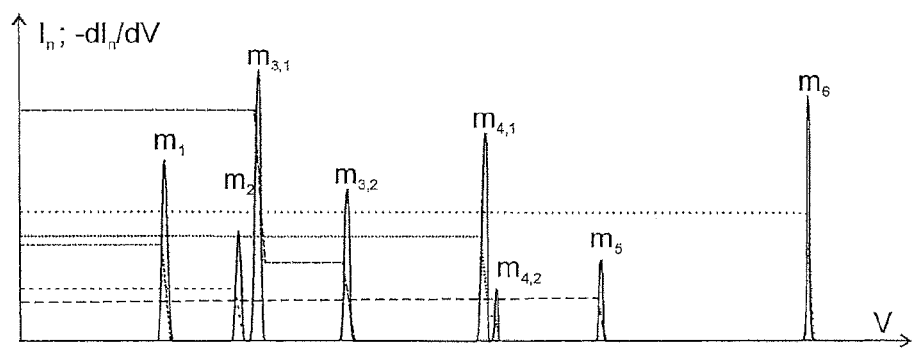
FIG. 7 graphically illustrates an acquisition of a mass-resolved mobility spectra of a similar ion mixture with a mass spectrometer coupled to the mobility spectrometer.
Figure 8:
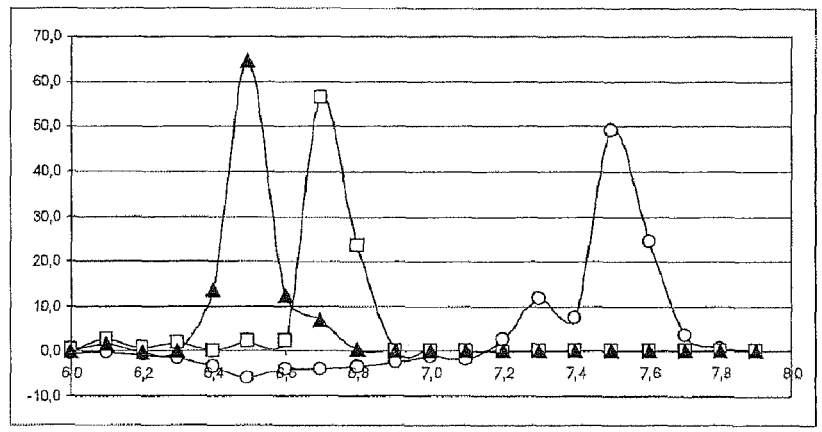
FIG. 8 graphically illustrates a measured mobility spectrum acquired using a combination of an ion mobility spectrometer and a mass spectrometer that does not include a Laval nozzle or a field barrier with a uniform height.

Relatively quick sequences of mass spectra may be acquired since the time-of-flight mass spectrometer operates with an acquisition rate of approximately 5,000 to 10,000 mass spectra per second. The mass spectra, however, merely include a few thousand ions and therefore have relatively high noise. A plurality of successive individual mass spectra therefore may be added together to form sum mass spectra. Approximately 25 to 100 mass spectra of good quality can be obtained in one second since adding together 100 to 200 individual mass spectra results in mass spectra with high signal-to-noise which can be evaluated relatively efficiently. The times of flight of the ion signals of the mass spectra are converted to masses, making it possible to obtain relatively accurate mass values with standard deviations of, for example, merely a few millionths of the mass (ppm) or better. From the series of mass spectra, the integral intensity curves $I_n = f(V)$ can be extracted for ions of individual masses $m_n$ (or individual mass ranges) as shown in FIG. 7. The derivative $dI_n/dV$, with respect to the height V of the field barrier, provides the mobility spectra for the ions. It is apparent therefore that several isomeric ion species with different structures or conformations can be present.

The chain of ion guides in the time-of-flight mass spectrometer in FIG. 5 includes a mass filter 43 and a collision cell 44. Such a time-of-flight mass spectrometer can also be used to acquire "daughter" ion mass spectra of selected ion species. In order to acquire daughter ion mass spectra, the "parent" ions are selected in the mass filter 43 before being fragmented in the collision cell 44. Since the mobility filter 41 can transmit both species of two isomeric ions or the species with the lower mobility, daughter ion spectra can be acquired either from the mixture of both species or from the single species allowed through. The daughter ion spectra may provide information on different structures or different conformations.

The mobilities measured using the aforedescribed methods provide extremely precise values for the mobility factor $K_0$, as long as the influence of the mobility factor $K_1$, which describes the influence of the field strength E on the form of the ions, can be neglected. It shall be emphasized here that precision measurements in drift regions and precision measurements at field barriers can deviate slightly from one another due to the influence of $K_1$. In drift regions, the drift velocity v of the ions is measured at a constant field strength E. At field barriers, in contrast, the field strength E, which produces a specific drift velocity v of around 780 meters per second, is measured. These field strengths, however, are comparable. In the drift regions, for example, the field strengths are constant at between 2 and 4 volts per millimeter, depending on setting. When the apertured diaphragms are each 4 mm apart, the voltages at field barriers are varied between 5 and 20 volts, and in some embodiments up to 32 volts, which are spread over the 8 millimeters separating the first and the third apertured diaphragms and thus result in a maximum of around 4 volts per millimeter (usually less) at the highest point of the field barrier.

The mobility spectra acquisition methods may be calibrated using known ion mobilities. The calibration function $K_0 = f(V)$ is substantially linear over wide ranges. After calibrating an acquisition method, the mobility spectra can be converted from the field barrier coordinates V to the mobility values $K_0$. From these calibrated spectra, the values $K_0$ for the mobilities of the individual ion species and the mobility resolution $R_{mob} = K_0/\Delta K_0$ of the method can be determined.

It is advantageous to use monoatomic helium as the drift gas for comparisons of measured mobility values $K_0$ with computed mobilities for different conformations of one ion species in order to simplify the calculations. Helium can be used as the curtain gas 22 in an electrospray ion source, passing together with the ions through the inlet capillary 23 into the vacuum system, where the Laval nozzle forms it into a supersonic gas jet.

Where no such comparison of measured and computed mobility values is planned, nitrogen, clean air or other gases can be introduced as the curtain gas 22 in the electrospray ion source to be used to form the supersonic gas jet. It should be noted, however, that nitrogen and other gases produce mobility values which are different than those of helium. A further advantageous gas for mobility measurements is argon.

The gas, used to form the supersonic gas jet, is added as curtain gas 22 in the electrospray ion source. The curtain gas takes up the ions and guides them through the inlet capillary 23 into the first stage of the vacuum system. The curtain gas 22 can be heated to around 200 to 300 degrees Celsius in order to contribute to the desolvation of the ions in the capillary. A relatively large drop in temperature may occur in the inlet capillary, and in the transitions of the differential pumping stages. A method has also been described, however, in which the curtain gas is cooled, for example, down to the temperature of liquid nitrogen, before being introduced into the inlet capillary. Advantageously, the cooled curtain gas can increase the mobility resolution. The temperature of the curtain gas can also be used to investigate temperature-dependent conformational changes of the ions as a result of changes to the folding.

The increase in mobility resolution is due at least in part to an almost complete absence of diffusion broadening of the ion signals. Any diffusion broadening of the ion signal that does occur before the field barrier is reached, however, has relatively no effect. Similarly, even after the ions have passed through the field barrier, diffusion broadening of the ion signals is typically only detrimental when the height V of the field barrier is rapidly changed. In these circumstances, therefore, the ions should be quickly guided to the ion detector or mass analyzer in order to reduce the diffusion broadening. On the way to the ion detector or mass spectrometer, however, the temperature of the adiabatically cooled gas jet is very low which strongly reduces the diffusion broadening.

The ion mobility spectra represent the distribution of the ions over different conformational or structural isomers. The structural isomers are usually relatively stable, and therefore are almost always measured in accordance with the structural isomers of the analyte molecules in the sample. Conformational isomers, on the other hand, can transform into other forms at higher temperatures. The distribution of conformational ions in the ion mobility spectrum shows how their original distribution in the sample may be modified by the processes in the ion source and, in further steps, by temperatures of the surrounding gases. Such transitions can be avoided, however, by carefully keeping the gas temperatures low. Alternatively, such transitions can be deliberately induced by temperature changes of the gases surrounding the ions in order to be investigated.

An advantage of the methods and instruments according to the present invention is the combination of high mobility resolution and the compact size of the necessary devices. A further advantage is that the necessary devices can easily be incorporated into a mass spectrometer.

Although the present invention has been illustrated and described with respect to several preferred embodiments thereof, various changes, omissions and additions to the form and detail thereof, may be made therein, without departing from the spirit and scope of the invention.

What is claimed is:

1. A method for dividing ions in a gas according to their mobility, comprising:
    forming a supersonic gas jet, having gas molecules with substantially equal velocities, by directing the gas through a Laval nozzle into an evacuated chamber;
    forming a field barrier, having a substantially uniform height across a cross-section of the supersonic gas jet, by respectively applying potentials $U_2$, $U_3$ and $U_4$ to an arrangement of three apertured diaphragms $R_2$, $R_3$ and $R_4$, which are respectively separated by distances $d_2$ and $d_3$, where $(U_4-U_3)/(U_3-U_2)=d_3/d_2$; and
    directing the ions in the supersonic gas jet against the field barrier, where ions with a mobility less than a mobility threshold are pushed over the field barrier, and where ions with a mobility higher than the mobility threshold are held back by the field barrier.

2. The method of claim 1, where the apertured diaphragms R2, R3 and R4 have substantially equal aperture diameters.

3. The method of claim 1, further comprising measuring an ion current of the ions pushed over the field barrier.

4. The method of claim 3, further comprising performing the measuring of the ion current with an ion detector without mass separation.

5. The method of claim 3, further comprising performing the measuring of the ion current with a mass analyzer.

6. The method of claim 4, further comprising:
    providing a continuous current of the ions from an ion source;
    pushing the ions with mobility less than the mobility threshold over the field barrier with the supersonic gas jet;
    measuring passing ions in the form of a total ion current curve as a function of the height of the field barrier; and
    generating a mobility spectrum by differentiating the total ion current curve.

7. The method of claim 5, further comprising:
    providing a continuous current of the ions from an ion source;
    pushing the ions with mobility less than the mobility threshold over the field barrier with the supersonic gas jet;
    measuring a series of mass spectra of passing ions as a function of the height of the field barrier;
    extracting ion current curves for ions of individual mass ranges from the mass spectra; and
    generating mass separated mobility spectra by differentiating the ion current curves.

8. The method of claim 7, further comprising:
    setting the height of the field barrier to measure fragment ion spectra of ions with lowest mobility; and
    lowering the field barrier to measure mixtures of ions of the lowest mobility and ions of higher mobility.

9. An ion mobility spectrometer, comprising:
    an ion source that generates ions in a gas in a high pressure region of the ion mobility spectrometer;
    a Laval nozzle that generates a supersonic gas jet from the gas with the ions in a lower pressure region of the ion mobility spectrometer;
    an arrangement of three or more apertured diaphragms $R_2$, $R_3$ and $R_4$ through which the supersonic gas jet moves axially, where the apertured diaphragms are respectively separated by distances $d_2$ and $d_3$;
    a power supply that respectively supplies the apertured diaphragms with potentials $U_2$, $U_3$ and $U_4$, where $(U_4-U_3)/(U_3-U_2)=d_3/d_2$; and
    an ion detector that measures a current of the ions passing the apertured diaphragms.

10. The ion mobility spectrometer of claim 9, where the Laval nozzle is located between a region maintained at atmospheric pressure and a first vacuum chamber, or in a wall located between two vacuum chambers of a differential pumping system.

11. The ion mobility spectrometer of claim 9, further comprising an additional RF quadrupole rod system located between the Laval nozzle and the arrangement of apertured diaphragms.

12. The ion mobility spectrometer of claim 9, where the ion detector comprises a mass spectrometer.

13. The ion mobility spectrometer of claim 12, where the mass spectrometer comprises a time-of-flight mass spectrometer with orthogonal ion injection.

14. An ion mobility spectrometer, comprising:
    an ion source that generates ions in a gas in a high pressure region of the ion mobility spectrometer;
    a Laval nozzle that generates a supersonic gas jet from the gas with the ions in a lower pressure region of the ion mobility spectrometer;
    a coaxial arrangement of three or more apertured diaphragms $R_2$, $R_3$ and $R_4$ through which the supersonic gas jet axially moves;
    a power supply that respectively supplies the apertured diaphragms with potentials $U_2$, $U_3$ and $U_4$ such that a field barrier is generated at the apertured diaphragm $R_4$ having a substantially uniform height across a cross-section of the supersonic gas jet, and such that ions in the supersonic gas jet are directed against the field barrier, where ions with a mobility less than a mobility threshold are pushed over the field barrier, and where ions with a mobility higher than the mobility threshold are held back by the field barrier; and
    an ion detector that measures a current of the ions passing the apertured diaphragms.

* * * * *